United States Patent [19]

Bonaldo

[11] Patent Number: 4,917,669
[45] Date of Patent: Apr. 17, 1990

[54] CATHETER INSERTER

[75] Inventor: Jean M. Bonaldo, Upland, Calif.

[73] Assignee: Safetyject, Costa Mesa, Calif.

[21] Appl. No.: 308,137

[22] Filed: Feb. 8, 1989

[51] Int. Cl.⁴ .............................................. A01M 5/00
[52] U.S. Cl. ..................................... 604/164; 604/198
[58] Field of Search .............. 604/168, 164, 198, 165, 604/110, 263, 156, 159

[56] References Cited

U.S. PATENT DOCUMENTS

| | | | |
|---|---|---|---|
| 4,747,831 | 5/1988 | Kulli | 604/198 |
| 4,832,696 | 5/1989 | Luthur et al. | 604/198 |
| 4,850,961 | 7/1989 | Wanderer et al. | 604/164 |

Primary Examiner—Stephen C. Pellegrino
Attorney, Agent, or Firm—Robert R. Thornton

[57] ABSTRACT

A catheter inserter has an inserter housing with a flat base and a cannula housing disposed within the inserter housing with a cannula extending generally parallel to the inserter housing longitudinal axis. Stop means are disposed at each end of the inserter housing. locking means on the cannula housing selectively engage the stop means to lock the cannula housing in a first disposition in which the cannula extends outwardly from the inserter housing and in a second disposition in which the cannula is retracted within said inserter housing. The cannula housing has a passage in fluid communication with the cannula which, together with means on the inserter housing and cannula housing, permit the external viewing of blood passing into the fluid passage from the cannula.

6 Claims, 2 Drawing Sheets

CATHETER INSERTER

BACKGROUND OF THE INVENTION

The present invention relates to a catheter inserter, that is, a device for inserting a catheter into the human body. Catheters have long been utilized in the medical profession and are designed for insertion into blood vessels and similar passageways or cavities in the body, to permit injection or withdrawal of fluids or to maintain the openness of an existing passageway into the existing vessel or cavity for subsequent injection or withdrawal of fluids. Various devices have been used for the insertion of catheters. All such devices have, in common, the use of a cannula, in order to make the original opening into the vessel or cavity. The catheter is normally mounted on the cannula and, when the cannula has pierced the vessel or cavity, the catheter is moved into position so as to maintain the opening when the cannula is withdrawn, and the cannula is thereafter withdrawn. Recently, it has become particularly desirable in order to avoid the spread of infection to ensure that the cannula, when withdrawn, is not exposed to prevent the cannula tip from piercing the flesh of the user or third parties during disposal.

BRIEF SUMMARY OF THE INVENTION

The present invention provides for a catheter inserter which has an inserter housing of parti-cylindrical cross-sectional configuration with a flat base generally parallel to the longitudinal axis of the inserter housing. A cannula is mounted on a hub which is a portion of a cannula housing disposed within the inserter housing and longitudinally slidable therewithin so that the cannula may be extended from and retracted into the inserter housing by selective longitudinal movement of the cannula housing. Stop means are provided to selectively lock the cannula housing in a cannula extended disposition, in which the cannula extends out of the inserter housing through an open end thereof, and in a cannula retracted disposition, in which the cannula is withdrawn completely into the interior of the inserter housing, so that the cannula tip is shielded by the exterior of the inserter housing. In the preferred embodiment, flashback viewing means are provided on the cannula housing and inserter housing so that the flow of blood or other fluid through the cannula into the interior of the catheter inserter through a fluid passage in communication with the cannula may be externally viewed in order to determine that the cannula has pierced the vein or other desired bodily element before the cannula is withdrawn, thereby leaving the catheter properly inserted.

BRIEF DESCRIPTION OF THE DRAWING

The present invention may be more readily understood by reference to the accompanying drawing, in which.

DETAILED DESCRIPTION OF THE PREFERRED EMBODIMENT

Figure 1:
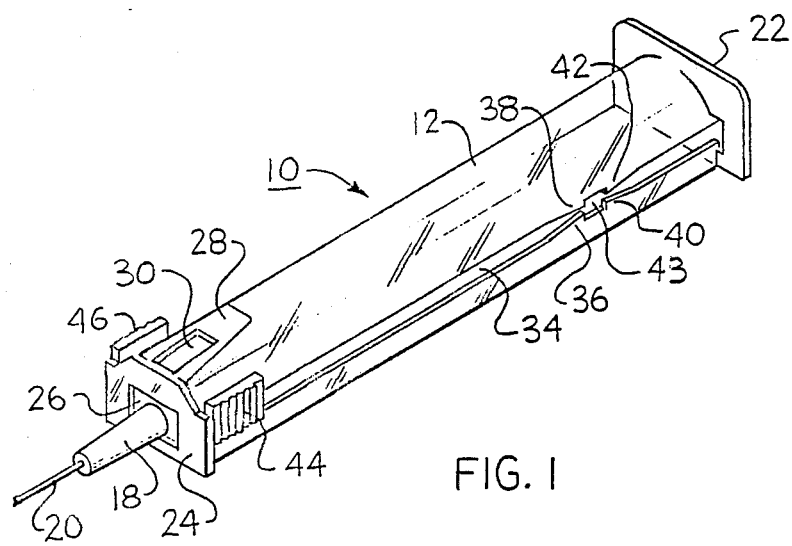
FIG. 1 is an isometric view of a catheter inserter according to the present invention with the cannula partially broken away.

Referring now to FIG. 1 there is show, an isometric view of a catheter inserter 10 according to the present invention. The catheter inserter 10 has an inserter housing 12 which may be made of any suitable material. Presently preferred is a transparent medical grade of polypropelene. Disposed within the inserter housing 12 is a cannula housing 14 (not shown, see FIG. 2) which may be made of any suitable material, such as a medical grade of polycarbamate. The cannula housing 14 has a hub portion 16 from which a cannula hub 18 extends. A cannula 20 is fixed to the cannula hub so as to extend therefrom.

The inserter housing 12 is parti-cylindrical in configuration. By parti-cylindrical is meant an elongated somewhat cylindrical body having a cross-sectional configuration such that a significant portion thereof is arcuate and a significant portion thereof is flat. The cannula housing 14 is also parti-cylindrical in configuration, and is sized so as to be complementary to the parti-cylindrical configuration of the inserter housing 12, within which the cannula housing 14 is disposed. The inserter housing 12 has a back plate 22 which closes the back end of the catheter inserter 10 and a front plate 24 which closes the front end of the inserter housing 12. The front plate 24 has a generally rectangular aperture 26 formed therein through which the cannula hub 18 extends. The inserter housing 12 has a flat 28 formed on the arcuate portion of the parti-cylindrical inserter housing 12 adjacent the front plate 24. A viewing aperture 30 is formed in the flat 28. A generally complementary cannula housing flat 32 is formed at the front end of the cannula housing 14, preferably in the hub portion 16, so as to underlie the viewing aperture 30. The inserter housing aperture 26 and cannula housing flat 28 are utilized to permit the external viewing of flashback occurring when fluid, such as blood, passes through the cannula into the housing body, as will be described hereinafter more specifically with respect to FIG. 3.

The inserter housing 12 has a longitudinal slot 34 formed along one side thereof, preferably at the termination of the arcuate portion of the cross-sectional configuration of the inserter housing 12. At the portion of the longitudinal slot 34 in proximity to the back plate 22, a first ramp 36 is formed in the slot 34 along its lower edge so as to narrow the width of the slot 34 in the direction of the back plate 22 by having the first ramp inclined away from the front plate 24. A second ramp 38 is formed along the opposite side of the slot 34 from the first ramp 36 so as also to be inclined away from the front plate 24 and further narrow the width of the longitudinal slot 34. The first and second ramps 36 and 38 are preferably mirror images of one another. A third ramp 40 is disposed on the lower side of the longitudinal slot 34 so as to be displaced rearwardly from the first ramp 36. A fourth ramp 42 is similarly formed on the upper side of the longitudinal slot 34 so as to constitute a mirror image of the third ramp 40.

Shown in FIG. 1 as adjacent the front plate 24 are a pair of serrated tabs 44 and 46 which are utilized in conjunction with the human hand to retract the cannula 20 into the inserter housing 12, as will be described hereinafter. For purposes of clarity, only one longitudinal slot 34 has been shown in FIG. 1. However, in the preferred embodiment, a slot which is the mirror image thereof is formed in the opposite side of the inserter housing 12, through which slot the serrated tab 46 is seen.

Figure 2:
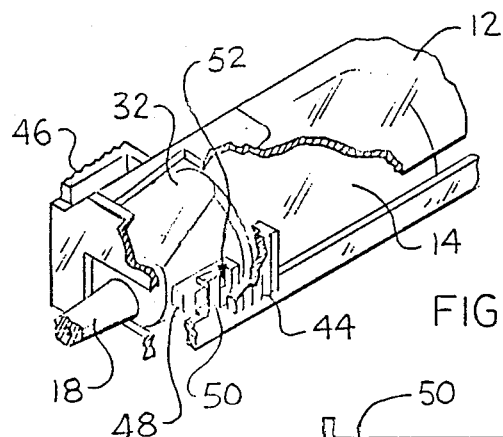
FIG. 2 is a partial sectional view of a portion of the cannula inserter of FIG. 1.

Referring now to FIG. 2, there is shown in greater detail the structure by which the serrated tab 44 and 46 are connected to the catheter inserter 10. As will be seen in FIG. 2, the serrated tab 44, at its end remote from the front plate 24, is connected directly to the cannula housing. Tab 44 has a locking plug 48 on extending inwardly therefrom. A locking stem 50 formed on the inserter housing 12 engages the locking lug 48 in a recess 52 formed therein. Normally, the engagement between the locking lug 48 and the locking lug recess 52 hold the inserter 10 in the disposition shown in FIG. 1 of retraction against the cannula 20 by rearward movement of the cannula housing 14 toward the back plate 22. However, pressure on the serrated tabs 44, 46 inwardly toward the longitudinal axis of the catheter inserter 10 permits the locking lugs 48 to clear the locking stem 50, thereby freeing the cannula housing from the locking disposition shown in FIG. 2 so that manual rearward pressure on the serrated tabs 44, 46 moves the cannula housing 14 toward the back plate 22 so as to retract the cannula 20 into the inserter housing 12.

Figure 3:
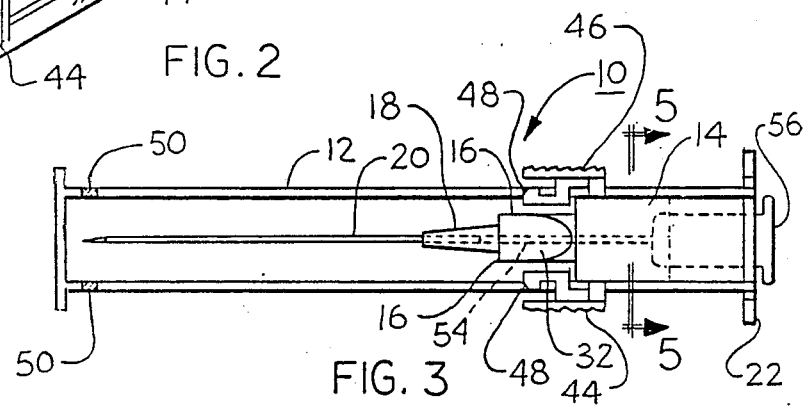
FIG. 3 is a plan view, partially in section, of the catheter inserter of FIG. 1 with the cannula in its retracted disposition.
Figure 4:
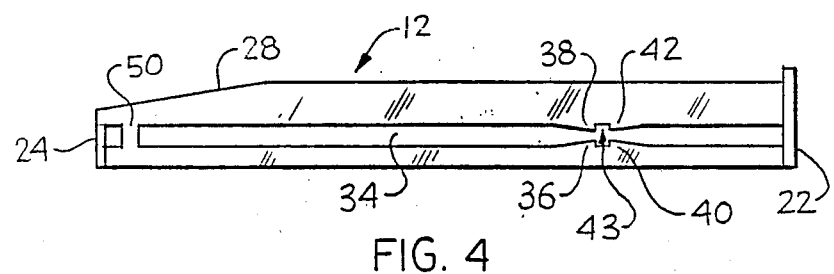
FIG. 4 is a side elevational view of the inserter housing utilized for the catheter inserter of the present invention.

Referring now to FIG. 3, the catheter inserter 10 is shown with the cannula 20 fully retracted within the inserter housing 12. In the disposition shown in FIG. 3, the locking lug 48 has overridden the first and second ramps 36 38, which are inclined toward the front plate, and abuts the back surfaces of the third and fourth ramps 40, 42, which are inclined away from the back plate 22. Thus, the locking lug 48 is locked in a slot 43 formed between the ramps 36, 38, 40, 42.

In FIG. 3, the cannula 20 is shown as extending into the cannula hub 18 and terminating short of the cannula housing hub portion 16. A fluid passage 54, shown in dotted lines, continues through the hub portion 16 and the cannula housing 14 to provide fluid communication between the cannula 20 and a filter plug 56 which extends through the back plate 22 and is press fit into the cannula housing 14. The purpose of the filter plug 56 is to provide pressure relief in the fluid passage 54 so that blood or other body fluid may pass through the cannula 20 into the fluid passage 54 under the cannula housing flat 32.

Since the cannula hub portion 16 is made of transparent material, this fluid flow, know as "flash back", may be viewed through the viewing aperture 30 in the inserter housing 12 when the catheter inserter 10 is in the disposition shown in FIG. 1. At the time when such flash back is seen, it is appropriate to remove the cannula 20 from the catheter being inserted (see FIG. 6) and withdraw the catheter inserter 10 from a catheter 62, as will be described hereinafter. Consequently, the filter plug 56 may be made of any appropriate material which will permit the pressure equalization between ambient pressure and the pressure existing within the cannula upon insertion into the human body.

Figure 5:
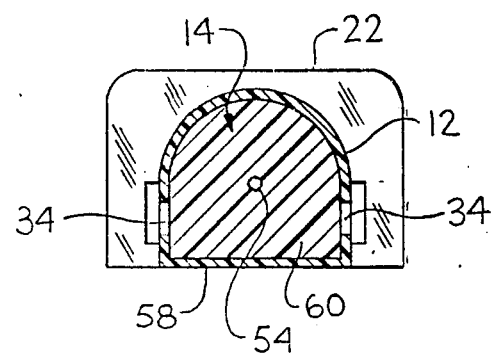
FIG. 5 is a view, in section, taken along lines 5—5 of FIG. 3.

Referring now to FIG. 5, there is shown in cross-section the catheter inserter 10 in a view taken along lines 5—5 of FIG. 3. As seen in FIG. 5, the fluid passage 54 is centrally disposed within the cannula housing 14 which, in turn, is disposed within the inserter housing 12. As is seen in FIG. 5, the cannula housing 14 has a cross-sectional configuration, in its main body portion, which is generally complementary to the cross-sectional configuration of the inserter housing 12. The flat base 58 of the inserter housing 12 serves to permit the catheter inserter to lie flat on the patient's body surface, for example a hand or arm, thereby diminishing, if not eliminating, one of the disadvantages of such prior devices in requiring the inserter to be taped to the body of the patient. The use of tape in this instance is both unsanitary and undependable, as well as requiring the tape to be removed before the inserter can be withdrawn from the catheter.

Figure 6:
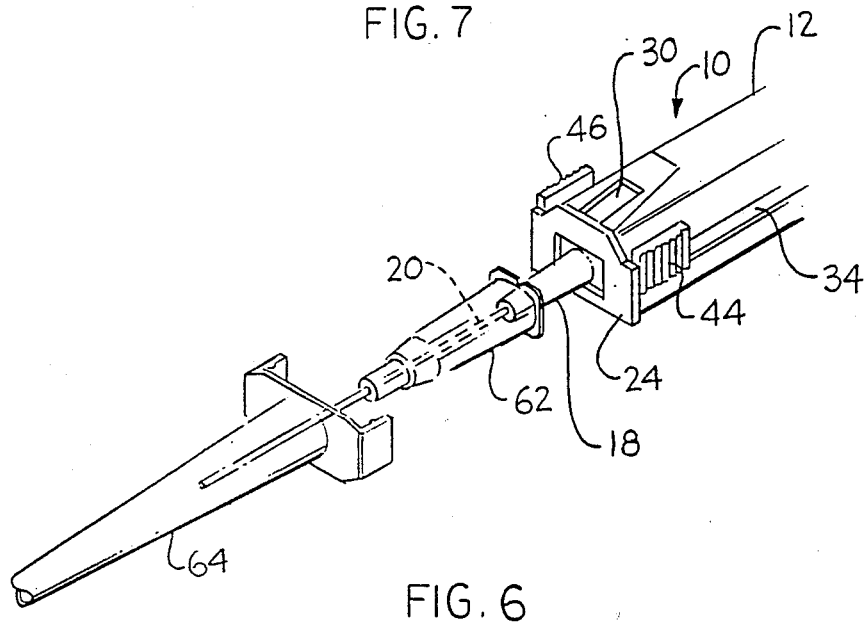
FIG. 6 is a partial exploded view of the catheter inserter of the present invention illustrating the relative disposition of the cannula, the catheter, and a protective sheet or cover utilized to shield both prior to use.

Referring now to FIG. 6, there is shown a partial exploded view of the catheter inserter 10, together with a catheter 62 and a safety shield 64 which, during storage and shipment, is placed over the catheter 62 and engages the front plate 24 so as to cover the serrated tabs 44, 46 to prevent accidental withdrawal of the cannula 20 into the inserter housing 12. The safety shield also serves to maintain the safety of the device, during handling, with respect to accidental sticking of the cannula tip into either the patient or the medical personnel involved in handling the devices.

Figure 7:
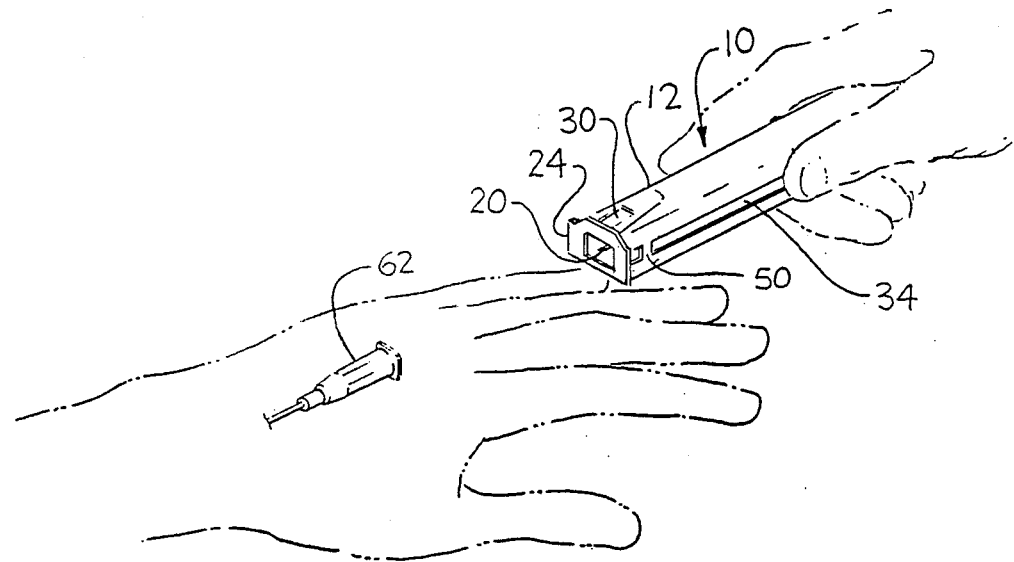
FIG. 7 is an isometric view illustrating the relative disposition of the catheter inserter and catheter upon retraction of the cannula into the inserter housing.

Referring now to FIG. 7, there is shown an isometric view, partially in section, of the catheter 62 inserted into the hand of a patient, shown in dotted lines, with the catheter inserter 10, having the cannula 20 already withdrawn into the inserter housing 12, having been removed from the proximity of the catheter 62. After such removal, the catheter inserter 10 is then disposed of in any conventional fashion, without danger of spreading infection or the like through accidental sticking of personnel with the cannula 20, since the cannula 20 is completely enclosed within the inserter housing 12 and locked in such withdrawn position by the engagement of the locking lug 48 with the locking slot 43.

One of the principal advantages of the present invention over prior art devices is the utilization of a first lock means at the open end of the inserter housing 12, and a second lock means:adjacent the closed end of the inserter housing 12. Conventional devices have used a single inserter housing lock, with two lock means formed in the cannula housing. Such a structure, upon retraction of the cannula into the inserter housing, results in the cannula housing extending a significant distance out of the rear of the inserter housing. Such an elongated structure may be subject to failure during disposal handling. This danger is eliminated by the present invention, in which, in the preferred embodiment, a cannula housing is always disposed substantially completely within the inserter housing, both in the cannula extended disposition and in the cannula retracted disposition. Thereby, a shorter overall structure is provided in the cannula retracted position, while still insuring that the device is not subject to failure, during disposal handling, with the consequent danger of piercing by the contaminated needle of personnel involved in the disposal.

The invention claimed is:

1. A catheter inserter comprising:

an inserter housing of parti-cylindrical configuration having a flat base which is generally parallel to the longitudinal axis of the inserter housing;

a cannula;

a cannula housing disposed within the inserter housing and longitudinally slidable therewithin, said cannula housing having a main body portion of a cross-sectional configuration which is generally complementary with the inserter housing cross-sectional configuration;

said cannula housing including hub means for fixing said cannula to said cannula housing main body so as to extend generally parallel to the inserter housing longitudinal axis;

first stop means disposed at said first end of said inserter housing;

locking means formed on said cannula housing so as to be selectively engageable with said first stop means to lock said cannula housing in a first disposition in which the cannula extends outwardly from the inserter housing at a first end of said inserter housing; and second stop means formed on said inserter housing remote from said first stop means and selectively engageable with said locking means to lock said cannula housing in a second disposition in which said cannula is retracted within said inserter housing.

2. A catheter inserter according to claim 1, and in which:

said inserter housing has a longitudinal slot formed along one side thereof so as to be displaced from said flat base;

said locking means includes a locking arm fixed to the cannula housing so as to extend outwardly from the inserter housing through the longitudinal slot; and said second stop means includes a ramp formed on one side of the longitudinal slot remote from the first end and inclined away therefrom, whereby movement of the locking arm away from the inserter housing first end so as to retract the cannula within the inserter housing causes the locking arm to override the ramp and become locked thereby against movement toward the inserter housing first end, thereby locking the cannula within the inserter housing.

3. A catheter inserter according to claim 1, and in which:

said inserter housing has a longitudinal slot formed along one side thereof so as to be displaced from said flat base;

said first stop means includes a locking stem extending transversely across the longitudinal slot adjacent to said first end;

said locking means includes a locking arm fixed to the cannula housing so as to extend outwardly from the inserter housing through the longitudinal slot; and said locking arm includes a locking recess formed therein so as to be engageable with said locking stem to selectively lock said cannula housing in said first disposition, said locking arm being of a cantilever-type configuration whereby digital pressure thereon normal to the inserter housing longitudinal axis causes the locking recess to move inwardly away from the locking stem so as to permit longitudinal movement of the cannula housing away from the inserter housing first end to move the cannula into the inserter housing.

4. A catheter inserter according to claim 3, and in which the second stop means includes a ramp formed on one side of the inserter housing longitudinal slot remote from the first end and inclined away therefrom, whereby movement of the locking arm away from the inserter housing first end so as to retract the cannula within the inserter housing causes the locking arm to override the ramp and become locked thereby against movement toward the inserter housing first end, thereby locking the cannula within the inserter housing.

5. A catheter inserter according to claim 3, and in which the inserter housing has a first pair of oppositely facing ramps formed along one side of the longitudinal slot so as to be inclined away from one another to form a locking slot therebetween remote from the first end and a second pair of ramps formed along the other slot side opposite the first pair of ramps so as to be mirror images thereof, whereby movement of the locking arm away from the inserter housing first end so as to retract the cannula within the inserter housing causes the locking arm to override the two ramps closest to the first end and become locked in the locking slots, thereby locking the cannula within the inserter housing.

6. A catheter inserter as in any one of the preceding claims, and in which the cannula housing has a passage formed therein so as to be in fluid communication with the cannula; and means on said inserter housing and said cannula housing to permit the external viewing of blood passing into the fluid passage from the cannula.

* * * * *